United States Patent [19]
Barish

[11] Patent Number: 5,473,662
[45] Date of Patent: Dec. 5, 1995

[54] RADIOGRAPHIC INSTRUMENT FOR OSSEOINTEGRATION IMPLANT

[76] Inventor: Elliott M. Barish, Crystal House, Suite 1F, 12 Old Mamaroneck Rd., White Plains, N.Y. 10605

[21] Appl. No.: 290,536

[22] Filed: Aug. 15, 1994

[51] Int. Cl.⁶ .................................................. A61B 6/14
[52] U.S. Cl. ........................... 378/170; 378/205; 433/72
[58] Field of Search ........................ 378/170, 167, 378/168, 169, 205, 204; 433/72, 75, 173, 174, 175, 176, 229

[56] References Cited

U.S. PATENT DOCUMENTS

| | | |
|---|---|---|
| 1,434,894 | 11/1922 | Hawkins . |
| 1,657,230 | 1/1928 | Simonton .............................. 378/170 |
| 1,899,877 | 2/1930 | Martin . |
| 3,092,721 | 6/1963 | Medwedeff et al. . |
| 3,436,826 | 4/1969 | Edelman ................................ 433/75 |
| 3,952,414 | 4/1976 | Shovers et al. . |
| 4,592,084 | 5/1986 | McAuslan . |
| 5,090,047 | 2/1992 | Angotti et al. . |
| 5,113,424 | 5/1992 | Burdea et al. . |
| 5,119,410 | 6/1992 | Donato . |
| 5,208,845 | 5/1993 | Gelb . |

FOREIGN PATENT DOCUMENTS

| | | | |
|---|---|---|---|
| 0073660 | 6/1948 | Norway | ................................ 378/170 |

Primary Examiner—David P. Porta

[57] ABSTRACT

A device which establishes alignment between a dental fixture implanted in the mouth of a patient and a dental instrument outside of the mouth includes a first portion insertable into the mouth and adapted for attachment to the fixture, and a second portion extending from the mouth in predetermined spatial relation to the first portion, the second portion facilitating alignment of the dental instrument to the fixture.

20 Claims, 3 Drawing Sheets

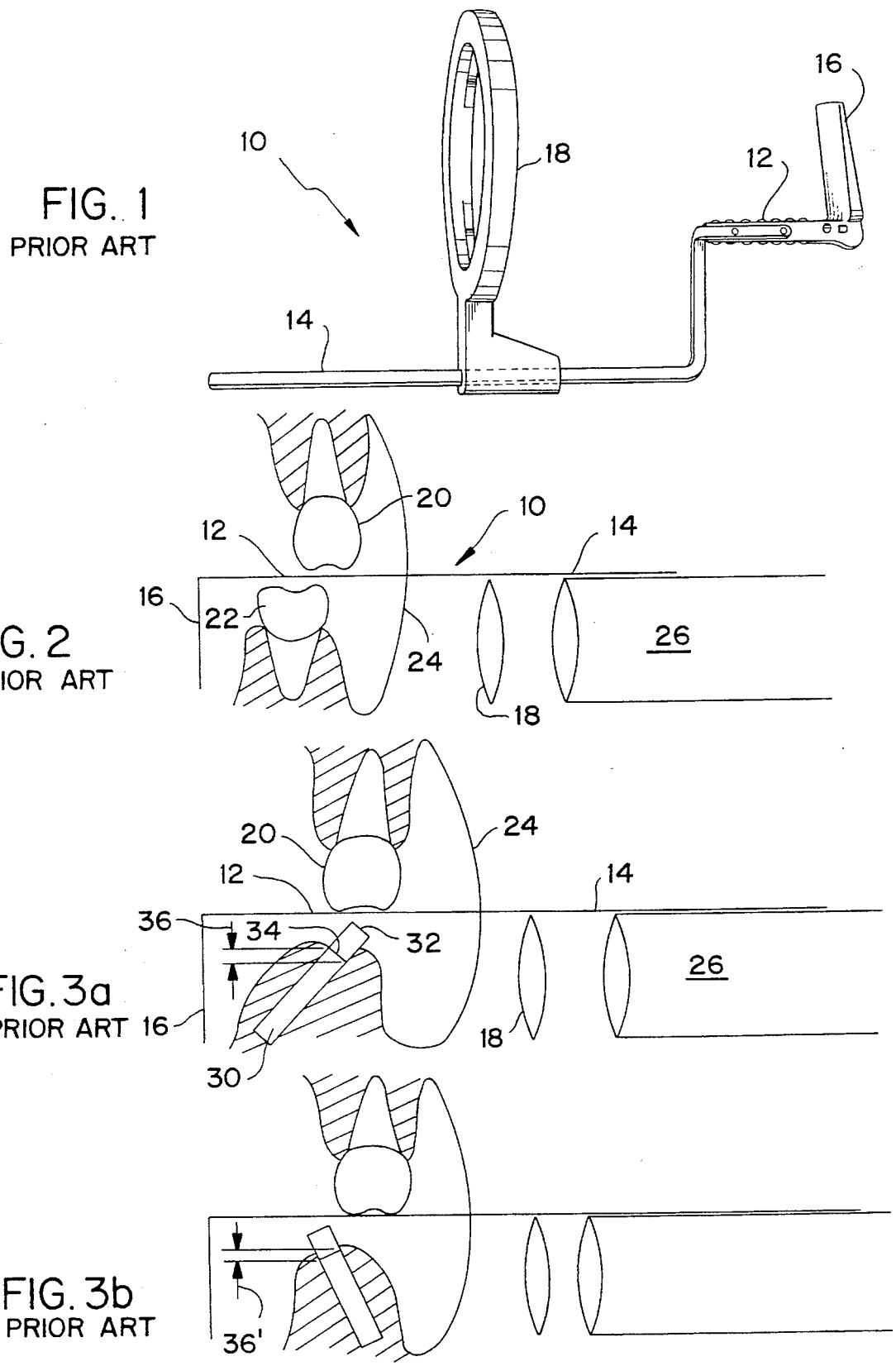

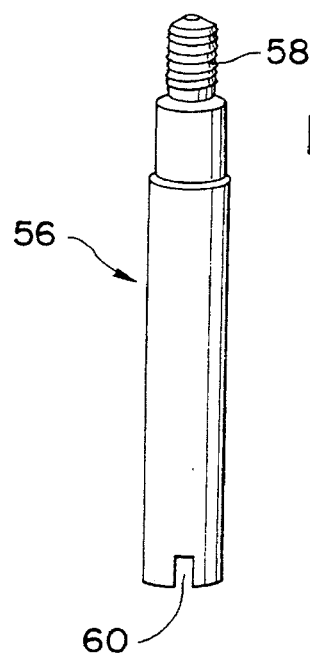
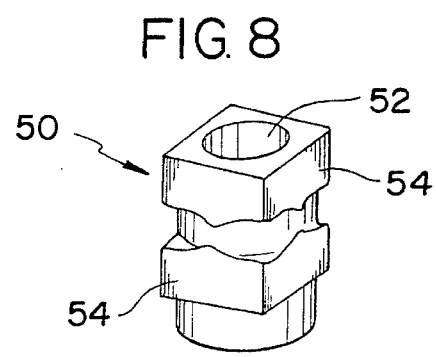
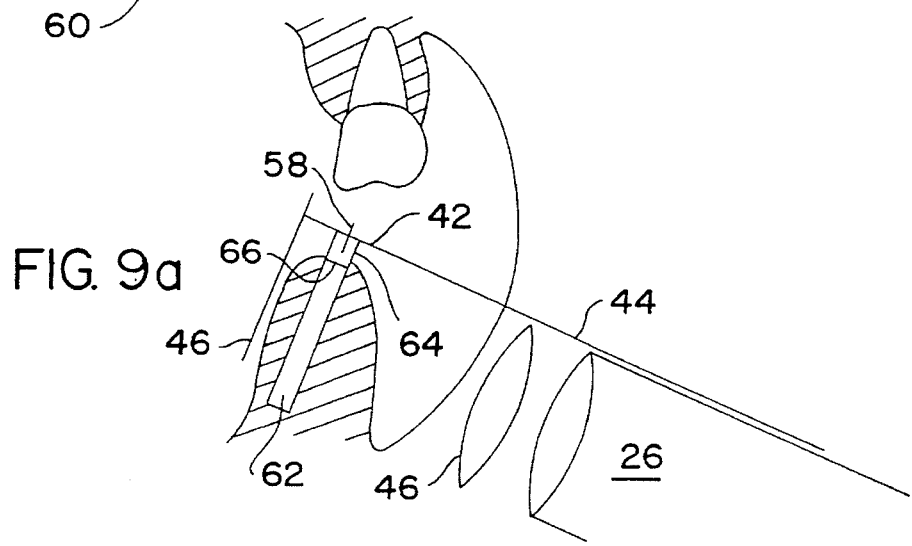
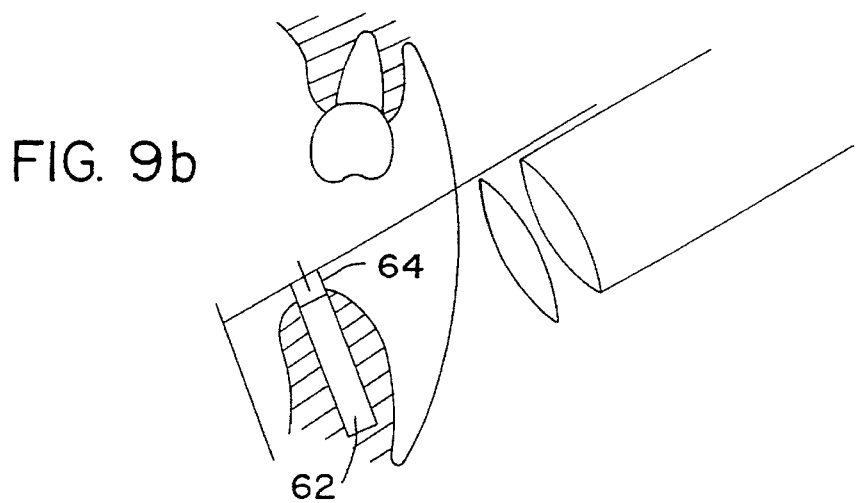

RADIOGRAPHIC INSTRUMENT FOR OSSEOINTEGRATION IMPLANT

BACKGROUND OF THE INVENTION

This invention relates to an instrument for aiding in radiography, particularly in radiography associated with osseointegration implant dentistry.

When restoring dentition where there is one or more teeth missing from the mouth of a patient, a modern technique may be used which is called implant dentistry. Implant dentistry relies upon the bonding of an implant to, for example, the jawbone of a patient. A bore is formed in the bone by drilling, and a part of an implant called a fixture is secured in the bone. The gums may then be sutured and, over a period of months, a bond forms between the bone and the fixture through osseointegration. After the fixture is secure in the bone, the gums are surgically opened and a restoration-supporting abutment is secured to the fixture. Ultimately, a restoration, such as an artificial tooth, is secured to the abutment.

If the abutment does not fit properly on the fixture, fracture or other failure of the restoration may result. Implantologists typically take x-rays of the implant to check the fit of an abutment on an implant fixture to avoid such problems. However, it has proven to be problematic for implantologists to take accurate and predictable radiographs (x-rays) to check the fit of an abutment on an implant fixture inasmuch as there have, to date, been no techniques or available instruments to consistently establish an appropriate parallel spatial relationship between the radiograph and the implant components.

The present invention provides an instrument which establishes a proper spatial relationship between implant components in the mouth of a patient and a radiographic device for producing x-ray images. Thus, a device according to the present invention overcomes the above-described problems heretofore encountered.

An instrument according to the present invention enables an implantologist to generate accurate and predictable radiographs comprising reliable images of implant components. Based upon such images, implantologists can evaluate, with a high degree of confidence, the condition of the implant components, thereby producing soundly-constructed dental restorations in a more consistent manner.

SUMMARY OF THE INVENTION

The present invention comprises an instrument or device for overcoming the above-described difficulties encountered in the prior art. More particularly, the present invention comprises a device which establishes a desired alignment between implant components in the mouth of a patient and a dental instrument outside of the mouth. A device according to the invention comprises a first portion insertable into the mouth, means for attaching the first portion to an implanted fixture, a second portion which extends from the mouth in a predetermined spatial relation to the first portion, and means associated with the second portion for aligning a dental instrument or apparatus which is external of the mouth to the fixture. The dental instrument or apparatus external of the mouth may be a radiographic apparatus.

According to a preferred embodiment of the invention, the device may be secured to the fixture when the device is in use. Means for attaching the first portion to the fixture may comprise means for threadedly engaging the fixture.

In a preferred form, a device according to the invention may also include a film holder for holding x-ray film for creating an x-ray image of the implant components.

In a particular embodiment disclosed in this application, the implant components comprise an implant fixture and an abutment which attaches to the fixture. In this embodiment, the device of the invention attaches to the abutment.

BRIEF DESCRIPTION OF THE DRAWINGS

The present invention will be better understood in light of the detailed description hereinbelow of a preferred embodiment thereof, considered together with the accompanying drawings in which:

FIG. 1 illustrates a known device for use in dental radiography;

FIG. 2 schematically illustrates the manner in which a device, such as shown in FIG. 1, may be used in dental radiography;

FIGS. 3a and 3b schematically illustrate the manner in which a device such as illustrated in FIG. 1 might be used in creating radiographic images of implant components;

FIG. 7 illustrates a guide pin for use in connection with the instrument shown in FIGS. 4–6;

FIG. 8 illustrates a form of coping which may be used in connection with the instrument shown in FIGS. 4–6; and FIGS. 9a and 9b schematically illustrate the manner in which an instrument according to the invention may be used for creating radiographic images of implant components.

DESCRIPTION OF A PREFERRED EMBODIMENT

Figure 4:
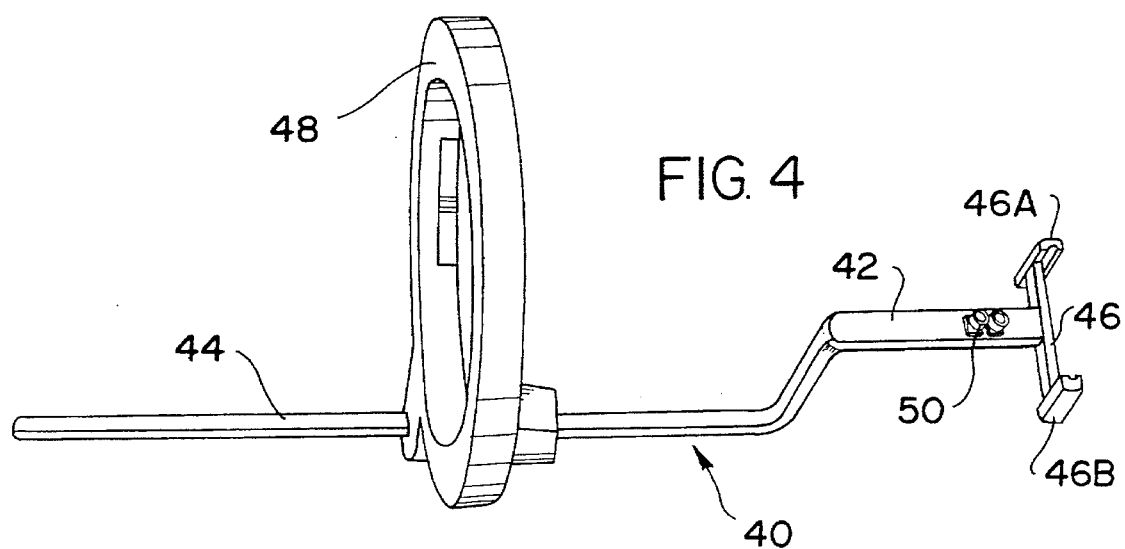
FIG. 4 is a perspective view of an instrument according to the present invention.

An understanding of the present invention will be greatly facilitated by an initial understanding of the existing technology and the problems associated therewith when known devices are used in connection with osseointegration implant dentistry.

FIG. 1 illustrates a known instrument which may be used when making oral radiographic images. The instrument illustrated in FIG. 1 corresponds generally to a Rinn XCP Anterior Instrument available from Rinn Corporation of Elgin, Illinois. The instrument, which is generally designated by reference numeral 10, comprises an intra-oral portion 12, and an extra-oral extension 14. An x-ray film holder 16 is associated with intra-oral portion 12. An aiming ring 18 is associated with extra-oral extension 14. Aiming ring 18 may be slidable upon extra-oral extension 14.

FIG. 2 schematically shows how a device as shown in FIG. 1 may be used to create x-ray images of tooth and gum structures. In use, intra-oral portion 12 of device 10 is inserted in the mouth of a patient. X-ray film, such as size 0 x-ray film, is inserted in film holder 16. Intra-oral portion 12 is held firmly between the upper and lower teeth 20 and 22, respectively, of the patient.

Extra-oral extension 14 extends outwardly beyond the cheek 24 of the patient in a predetermined spatial relationship with intra-oral portion 12. Portion 14 thus supports aiming ring 18 in a pre-determined spatial relationship to teeth 20, 22 and film holder 16. This assists an operator in aligning a radiographic apparatus 26, such as an x-ray cone, with aiming ring 18 and, thus, with film in holder 16 and the tooth and gum structures of the patient. Therefore, radiation can be predictably emitted by apparatus 26 along an appropriate path to create a properly oriented image of the patient's dental structures on film in holder 16.

The above-described use of a device such as shown in FIG. 1 is generally satisfactory for making x-ray images of tooth structures in most normal circumstances. However, it is generally not suitable for osseointegrated implants. Specifically, at the stage of osseointegrated implant surgery when an abutment is attached to an implant fixture, it is necessary for the dental surgeon to take radiographs to confirm the successful integration of the fixture with the bone, as well as the proper fitting of the abutment on the fixture. Two radiographs must be taken. If a periapical radiograph is used to check the state of osseointegration, it is not sufficient to ensure the fit of the abutment on the fixture because the radiograph may not be parallel to the implant components. Parallel alignment of the radiograph with the implant components (the fixture and abutment) is critical. The present invention provides a device to assure such parallelism.

FIGS. 3a and 3b illustrate the problem. FIG. 3a is a schematic illustration, corresponding generally to that of FIG. 2, with corresponding parts being similarly numbered. However, FIG. 3a illustrates a situation in which a lower tooth 22 is no longer present in the mouth of the patient, perhaps as the result of injury or disease.

In place of lower tooth 22, FIG. 3a illustrates a fixture 30 which has been implanted by a surgeon in the bone of the lower jaw. An abutment 32 is attached to fixture 30 for later attachment of a restoration.

When taking an x-ray to verify a proper fitting of abutment 32 to fixture 30, it is necessary to properly align the x-ray cone and film with the interface 34 between the abutment and the fixture. However, if the known instrument (FIG. 1) is held between the teeth of the patient, the cone 26 and film in holder 16 will generally not be aligned with interface 34 which is often tilted due to the fact that the fixture is not perfectly positioned vertically to the jaw. For illustration, fixture 30 and abutment 32 are shown in exaggerated misalignment in FIG. 3a.

A further problem which may occur in circumstances such as illustrated in FIG. 3a is that, due to one or more missing teeth, it may not even be possible for the patient to hold the known device at all in the manner illustrated and described.

FIG. 3a shows a buccaly inclined fixture 30. If the known device is held as described between teeth of the patient, a false positive relationship between fixture 30 and abutment 32 will appear in the resulting radiographic image due to an overlap region 36. This overlap region results from the fact that, viewed along the line of sight of radiographic cone 26, abutment 32 appears to overlap fixture 30 at interface 34. The same result occurs in the case of a lingually inclined fixture and abutment, as shown in FIG. 3b. In that case, an overlap region 36' again appears. Thus, the reliability of x-ray images is impaired, and the surgeon is left without sufficiently accurate information upon which to determine whether a satisfactory bond exists between the implant fixture and the abutment.

FIG. 4 illustrates a preferred embodiment of an instrument according to the present invention which overcomes the above-described problems and shortcomings.

An instrument 40 according to the invention comprises an intra-oral portion 42 and an extra-oral extension 44. An x-ray film holder 46 is associated with intra-oral portion 42. Film holder 46 comprises slotted arms 46A and 46B for holding x-ray film.

An aiming ring 48 is associated with extra-oral extension 44. Aiming ring 48 may be slidable upon the extra-oral extension.

The illustrated embodiment of the invention includes at least one fitting or coping 50 for facilitating attachment of the instrument to an implant. In the preferred embodiment illustrated, a standard abutment impression coping is employed, as will be described in greater detail hereinafter. This component is available from Implant Innovations, Inc. of West Palm Beach, Fla. It should be understood, however, that this component is selected to be compatible with a particular type of implant component. Each implant system could require a different fitting or coping to properly interface with and attach to the implant components.

Figure 5:
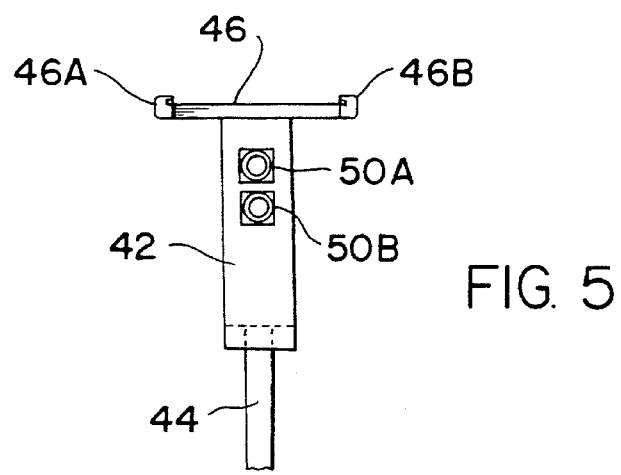
FIG. 5 is a top view of a portion of the instrument shown in FIG. 4.
Figure 6:
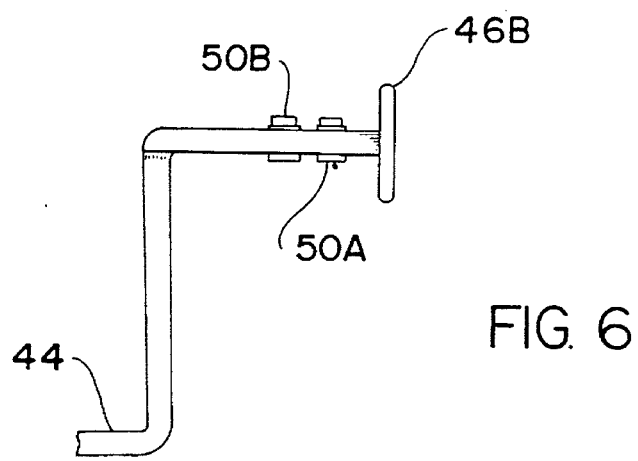
FIG. 6 is a side view of a portion of the instrument illustrated in FIG. 4, corresponding to the portion also illustrated in FIG. 5.

FIG. 5 is a top view of intra-oral portion 42 of the instrument of FIG. 4. FIG. 6 is a side view of the same portion of the instrument. As more clearly seen in these figures, the illustrated embodiment of the invention comprises two copings 50A and 50B. This permits some flexibility in attaching the instrument, depending upon the location of the implant in the mouth, as will be described in greater detail hereinafter.

FIG. 8 illustrates coping 50 in greater detail. Coping 50 comprises an aperture 52 and a pair of flanges 54. The flanges facilitate attachment of the coping 50 in openings in intra-oral portion 42.

FIG. 7 illustrates a guide pin 56 which is used in conjunction with coping 50 to attach the instrument of the disclosed embodiment of the invention to implant components. Guide pin 56 comprises a threaded end 58 and a slot 60 in the opposite end thereof. The diameter of pin 56 is such that it fits within aperture 52 of coping 50. In the particular embodiment illustrated, the abutment associated with the implant comprises a threaded aperture to receive end 58 of pin 56, as will be described with reference to FIGS. 9a and 9b.

FIG. 9a schematically illustrates an instrument 40 according to the invention in use in conjunction with an implant fixture 62 and an associated abutment 64. Intra-oral portion 42 is positioned over the implant with one of the copings 50 (not shown in FIG. 9a) directly over abutment 64. Depending upon the location of the implant components 62, 64 in the mouth, and depending also upon the size of the patient's mouth, either coping 50A or coping 50B might be used.

Pin 56 is then inserted through aperture 52 and threadedly engaged within abutment 64 via threaded end 58 mating with a threaded aperture (not shown) in the abutment. The result is that intra-oral portion 42 and, thus, extra-oral extension 44 and aiming ring 46, are fixed in a predetermined orientation with respect to the fixture, abutment and the interface 66 with the axis of extra-oral extension being parallel to interface 66. X-ray cone 26 can therefore be aligned using aiming ring 46, as described above. The result is that the x-ray cone and the film are reliably aligned parallel to the interface and an accurate and useful image can be created.

As a result of the features of the present invention, the x-ray cone and film positioned in film holder 46 will always be aligned in a proper manner with the fixture, abutment and the interface therebetween. The surgeon or technician will be able to reliably obtain an x-ray image along a line of sight parallel to interface 66, thereby obtaining a true image of the bond between abutment 64 and fixture 62.

This will be true regardless of the orientation of the implant, as shown in FIGS. 9a and 9b. In FIG. 9a, an implant is buccaly inclined. For purposes of illustration, the implant in FIG. 9a is misaligned in exaggerated fashion. Nevertheless, the film in holder 46 and the x-ray cone 26 are properly aligned along a path parallel to interface 66. The same is true in FIG. 9b wherein the implant fixture and abutment are lingually inclined.

Thus, the invention overcomes the problems associated with existing instruments. The invention enables a dental surgeon or technician to predictably and reliably create accurate images of implant components which enable the surgeon to determine, with a high degree of confidence, whether the components are satisfactory for further restorative procedures.

A single embodiment of the invention has been disclosed and illustrated. However, the invention is not limited to that embodiment. Generally, one anterior and two posterior instruments need to be fabricated in order for an operator to be able to radiograph an implant located anywhere in the mouth. Further, as suggested above, since every implant system has a different abutment, different radiographic instruments would have to be fabricated to interface with and attach to each type of abutment in respective systems.

Additionally, the particular size and arrangement of the x-ray film holder may be varied to enable the instrument to fit comfortably in various portions of a patient's mouth without interfering with adjoining tissues and dental structures.

The invention having been thus described with respect to a particular embodiment is not limited to that embodiment, but includes all variations within the scope of the appended claims.

I claim:

1. A device for establishing alignment between a fixture implanted in the mouth of a patient and a dental instrument, comprising
   a first portion;
   means for threadedly engaging said first portion to the fixture;
   a second portion in predetermined spatial relation to said first portion, said second portion comprising means for aligning a dental instrument to the fixture.

2. A device for establishing alignment between an implant in the mouth of a patient and a dental instrument, comprising
   a first portion;
   means for attaching said first portion to the implant;
   a second portion in predetermined spatial relation to said first portion, said second portion comprising means for aligning a dental instrument to the implant.

3. A device for establishing alignment between a dental fixture implanted in the mouth of a patient and a dental instrument outside of the mouth, comprising
   a first portion insertable into the mouth;
   means for attaching said first portion to the fixture;
   a second portion extending from the mouth and in predetermined spatial relation to said first portion; and
   means associated with said second portion for aligning a dental instrument external of the mouth to the fixture.

4. A device as in claim 3, wherein said means for attaching said first portion to the fixture comprises means for securing said first portion to the fixture.

5. A device as in claim 3, wherein the dental instrument is a radiographic apparatus, and said means for aligning comprises means for aligning the radiographic apparatus with the fixture.

6. A device as in claim 5, further comprising a film holder associated with said first portion, wherein said means for aligning comprises means for aiming the radiographic apparatus at said film.

7. A device as in claim 6, wherein said means for aligning comprises an aiming ring.

8. A device for establishing alignment between a fixture implanted in the mouth of a patient and a radiographic apparatus outside of the mouth, comprising
   a first portion insertable into the mouth;
   means for securing said first portion to the fixture;
   a film holder associated with said first portion;
   a second portion extending from said first portion and extending outside of the mouth; and
   an aiming member associated with said second portion for aligning said radiographic apparatus with the fixture in a predetermined spatial relationship.

9. A device as in claim 8, wherein said second portion is in a fixed spatial relationship to said first portion.

10. A device as in claim 8, wherein said aiming member is an aiming ring associated with said second portion.

11. A device for establishing alignment between a dental fixture implanted in the mouth of a patient and a dental instrument outside of the mouth, comprising
    a first portion insertable into the mouth;
    means for threadedly engaging said first portion to the fixture;
    a second portion extending from the mouth and in predetermined spatial relation to said first portion; and
    means associated with said second portion for aligning a dental instrument external of the mouth to the fixture.

12. A device as in claim 11, wherein said means for attaching comprises a fitting associated with said first part and a threaded member associated with said fitting and adapted to threadedly engage the fixture to thereby attach said first portion to the fixture.

13. A device for establishing alignment between a fixture implanted in the mouth of a patient and a dental instrument, comprising
    a first portion;
    means for attaching said first portion to the fixture;
    a second portion in predetermined spatial relation to said first portion, said second portion comprising means for aligning a dental instrument to the fixture.

14. A device as in claim 13, wherein said first portion attaches to the fixture in predetermined spatial relation.

15. A device as in claim 13, wherein said means for attaching said first portion to the fixture comprises means for securing said first portion to the fixture.

16. A device as in claim 13, wherein said second portion extends from the mouth of the patient.

17. A device as in claim 16, said second portion comprising an aiming ring for aligning a radiographic apparatus with the fixture.

18. A device for establishing alignment between an abutment implanted in the mouth of a patient and a radiographic apparatus outside of the mouth, comprising
    a first portion insertable into the mouth;
    means for securing said first portion to the abutment;
    a film holder associated with said first portion;
    a second portion extending from said first portion and extending outside of the mouth; and an aiming member associated with said second portion for aligning said radiographic apparatus with the abutment in a predetermined spatial relationship.

19. A device as in claim 18, wherein said abutment comprises means for mounting a dental restoration.

20. A device as in claim 19, wherein said device threadedly attaches to said abutment.

* * * * *